(12) United States Patent
Cisko, Jr. et al.

(10) Patent No.: US 8,728,048 B2
(45) Date of Patent: May 20, 2014

(54) MALE EXTERNAL CATHETER AND METHOD OF MAKING SAME

(75) Inventors: George J. Cisko, Jr., Spring Grove, IL (US); Seamus T. Kavanagh, Libertyville, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 11/913,524

(22) PCT Filed: Mar. 24, 2006

(86) PCT No.: PCT/US2006/010941
§ 371 (c)(1),
(2), (4) Date: Nov. 20, 2007

(87) PCT Pub. No.: WO2007/001526
PCT Pub. Date: Jan. 4, 2007

(65) Prior Publication Data
US 2008/0215021 A1    Sep. 4, 2008

Related U.S. Application Data

(60) Provisional application No. 60/690,718, filed on Jun. 15, 2005.

(51) Int. Cl.
*A61F 5/44*    (2006.01)
(52) U.S. Cl.
USPC .......................................... 604/349; 604/544
(58) Field of Classification Search
CPC ......... A61M 1/00; A61M 27/00; A61M 5/00; A61F 5/44
USPC ................... 604/349, 317, 327, 540; 249/142
See application file for complete search history.

(56) References Cited

U.S. PATENT DOCUMENTS 2,789,560 A * 4/1957 Weimer ........................ 604/349
3,339,551 A   9/1967 Stoutenhurgh ................ 128/295
3,385,553 A * 5/1968 Braun .......................... 249/142
3,880,282 A * 4/1975 Naumann ..................... 374/209

(Continued)

FOREIGN PATENT DOCUMENTS

EP       1 629 799 A1    3/2006
JP       11-513597 T     11/1999

(Continued)

OTHER PUBLICATIONS

International Search Report of International Application No. PCT/US06/10941, mailed Sep. 11, 2007.

(Continued)

*Primary Examiner* — Tatyana Zalukaeva
*Assistant Examiner* — Benedict L Hanrahan
(74) *Attorney, Agent, or Firm* — Cook Alex Ltd.

(57) ABSTRACT

A male external catheter formed of injection-moldable plastic material is disclosed, which has a neck section with inner and outer surfaces having substantially different contours. The male external catheter has a generally cylindrical body section, a drain tube section and the funnel-shaped neck section. The drain tube section has a smaller cross-section than the body section, and the funnel shaped neck section is interposed between and merges with the body and the drain tube sections. A method of manufacture of such a catheter is also disclosed.

36 Claims, 4 Drawing Sheets

(56) References Cited

U.S. PATENT DOCUMENTS

| | | | |
|---|---|---|---|
| 4,149,695 A * | 4/1979 | Quick et al. | 249/82 |
| 4,511,163 A | 4/1985 | Harris et al. | |
| 4,808,105 A | 2/1989 | Linss et al. | |
| 5,176,666 A | 1/1993 | Conway et al. | 604/349 |
| 5,205,298 A | 4/1993 | Hurst | 128/844 |
| 5,554,141 A * | 9/1996 | Wendler | 604/352 |
| 6,248,096 B1 | 6/2001 | Dwork et al. | 604/349 |
| 7,431,876 B2 * | 10/2008 | Mejlhede et al. | 264/328.1 |
| 2001/0005782 A1 | 6/2001 | Tanghoj et al. | 604/327 |
| 2002/0087130 A1 | 7/2002 | Guldfeldt et al. | 604/317 |
| 2005/0033237 A1 * | 2/2005 | Fentress et al. | 604/165.03 |
| 2005/0072432 A1 | 4/2005 | Kepp | 128/844 |
| 2009/0048570 A1 * | 2/2009 | Jensen | 604/349 |

FOREIGN PATENT DOCUMENTS

| | | |
|---|---|---|
| WO | WO-97/14353 A1 | 4/1997 |
| WO | WO-2004/065122 A1 | 8/2004 |
| WO | WO-2006/021220 A1 | 3/2006 |
| WO | WO-2006/024637 A1 | 3/2006 |

OTHER PUBLICATIONS

Written Opinion of the International Searching Authority of PCT/US06/10941, mailed Sep. 11, 2007.
Extended European Search Report for Application No. 06739623.4, dated May 17, 2010.
Preliminary Notice of Reasons for Rejection for Japanese Application No. 2008-516824, dated Apr. 20, 2011.

* cited by examiner

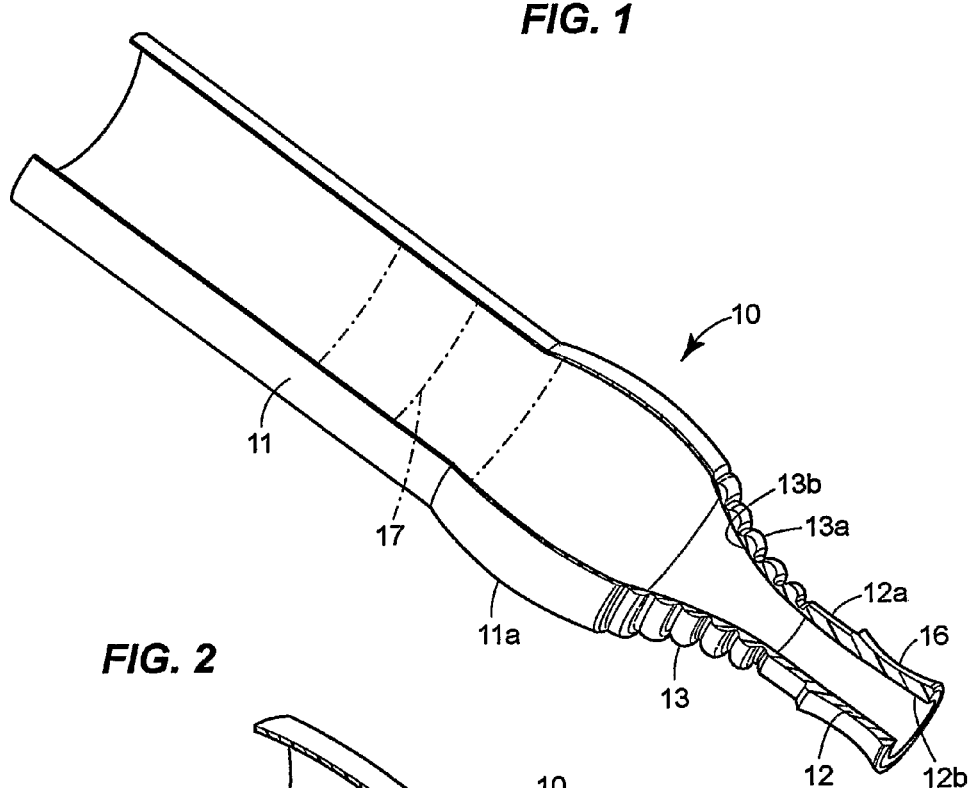
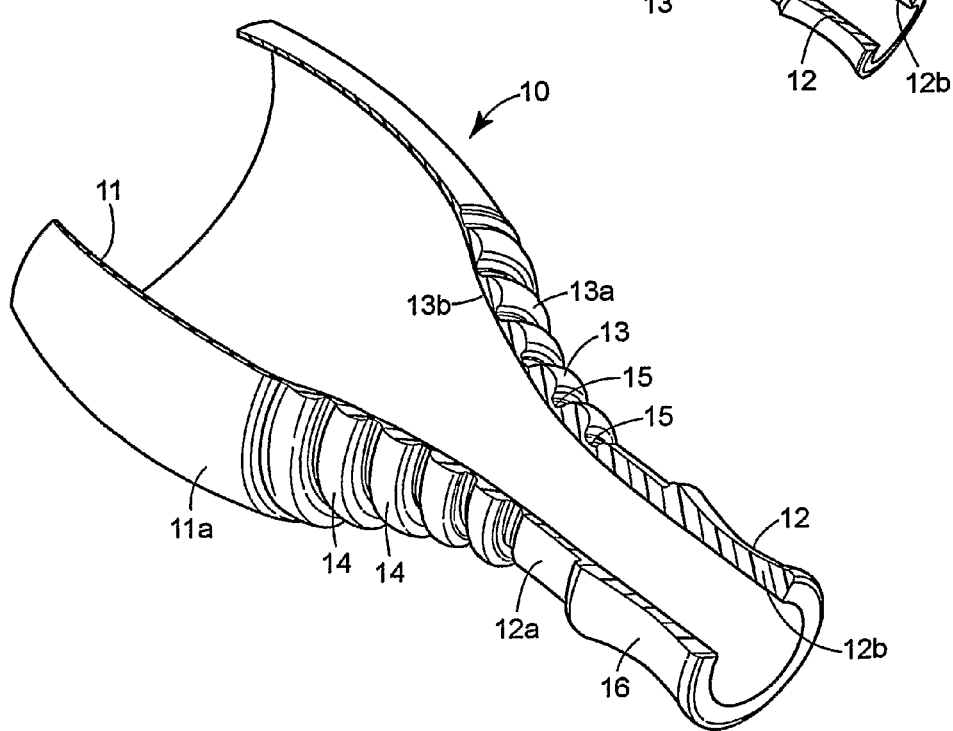

MALE EXTERNAL CATHETER AND METHOD OF MAKING SAME

CROSS REFERENCE TO RELATED APPLICATION

This application is the U.S. National Phase of PCT/US06/10941, filed Mar. 24, 2006, and claims the benefit of the filing date of U.S. Provisional Application No. 60/690,718, filed Jun. 15, 2005.

BACKGROUND OF THE INVENTION

Male external urinary catheters are commonly manufactured by dip processing or blow molding. Examples of dip processing are set forth in U.S. Pat. Nos. 5,376,085 (silicone rubber), U.S. Pat. No. 5,407,715 (triblock copolymers), U.S. Pat. No. 4,475,910 (latex), U.S. Pat. No. 4,846,909 (latex) and International Publication WO 96/29962 (polyurethane). A combination of injection molding, pull extrusion and blow molding is disclosed in U.S. Pat. No. 5,554,141 (styrene-based block copolymers). Regardless of the method used, the catheters produced by such processes characteristically have the common feature of inner surface contours that mimic or match the contours of the outer surfaces.

Typically, a male external catheter has a generally cylindrical body section or sheath that fits about a wearer's penis and may include a bulbous enlargement at it distal end for extending over the glands, a drain tube section of reduced diameter adapted to be connected to drainage tubing leading to a leg bag or some other urine-receiving receptacle, and a tapered or generally frusto-conical neck section interposed between and connecting the body and drain tube sections. The tapered neck section is frequently provided with a series of annular corrugations or convolutions to permit greater stretchability, bending and twisting of the neck section when the device is in use and to do so with less chance that kinking or obstruction of the lumen might occur. While the corrugations are effective in achieving those objectives, they also result in a construction in which the inner surface of the neck portion, which mimics the corrugations of the outer surface, has the disadvantage of collecting and retaining small amounts of urine within its annular channels or grooves.

The fact that inner and outer surfaces of conventional male external catheters are parallel to each other or follow the same contours also has other disadvantages. Such catheters commonly have smooth-walled drain tube sections that must be pushed over stepped connectors to attach the catheters to urine collection bags. Smooth-walled tubes can be difficult to push onto such connectors but, heretofore, it has not been considered feasible to provide such a drain tube section with a contoured outer surface that facilitates gripping and advancing the section onto a connector while at the same time providing such section with a smooth cylindrical inner surface.

SUMMARY OF THE INVENTION

This invention is concerned with a male external catheter and the method for its manufacture, in which the catheter is formed in whole or in part from a suitable injection-moldable plastic material and in which the contours of its inner and outer surfaces are selectively and substantially different. Thus, the outer surface of the funnel-shaped neck section may have a series of concentric corrugations, as described above, while the inner surface of that same section may be smoothly tapered, thereby enhancing flow and eliminating or reducing the possibilities that urine might collect and be retained in the neck section. Similarly, the outer surface of the drain tube section might be provided with one or more recesses and or projections to facilitate manual gripping of the drainage tube section when it is to be joined to a connector. Other substantial differences in the contours and textures of the inner and outer surfaces may be provided to facilitate application and use of the catheter.

An important aspect of this invention lies in providing a male external catheter that is formed entirely by injection molding and composed of one or more injection-moldable polymeric materials. In its method of manufacture, a mandrel having an outer surface that defines the inside surface of such a catheter is positioned within a multiple-section mold having an inner surface defining the contours of the catheter's outer surface. One or more molten plastic materials, usually but not necessarily thermoplastic elastomeric materials, are then injected into the cavity of the mold and, after cooling, the mold's outer sections are separated. The catheter may be retained on the mandrel for further processing or, if desired, it may be removed and repositioned on a working mandrel.

The production method has the advantages of providing a male external catheter having sections formed of different but compatible injection-moldable plastic materials. For example, the catheter may have a drainage tube section formed of a relatively rigid or stiff thermoplastic material (which may or may not be elastomeric) while the remaining sections may be formed of a compatible thermoplastic having the desired properties of softness and elasticity (i.e., stretchability and recoverability). Further, the sections may be formed in different colors, textures and/or degrees of transparency and gas (vapor) permeability. Such a catheter, having sections formed of different but compatible injection-moldable plastics, may be made using known over-molding or multi-shot injection molding techniques.

A further advantage of using injection molding, and particularly multi-shot molding or over-molding techniques, is that the catheter may be formed with materials of different composition along its inner and outer surfaces. For example, the outer layer may include additives to promote release whereas the inner layer may have additives to provide or at least promote adhesion, or enhance skin care, or supply therapeutic and/or antibacterial agents to the skin.

Other features, objects and advantages of the invention will become apparent from the drawings and specification.

BRIEF DESCRIPTION OF THE DRAWINGS

FIG. 1 is a longitudinal side view of a male external catheter embodying this invention, a portion of the catheter being cut away to reveal the cross sectional contours of the product.

FIG. 2 is an enlarged perspective view of the neck and connected drain tube sections of the catheter, again with a portion of the catheter removed to reveal the differences between the contours of the catheters inner and outer surfaces.

DETAILED DESCRIPTION OF PREFERRED EMBODIMENTS

Figure 3:
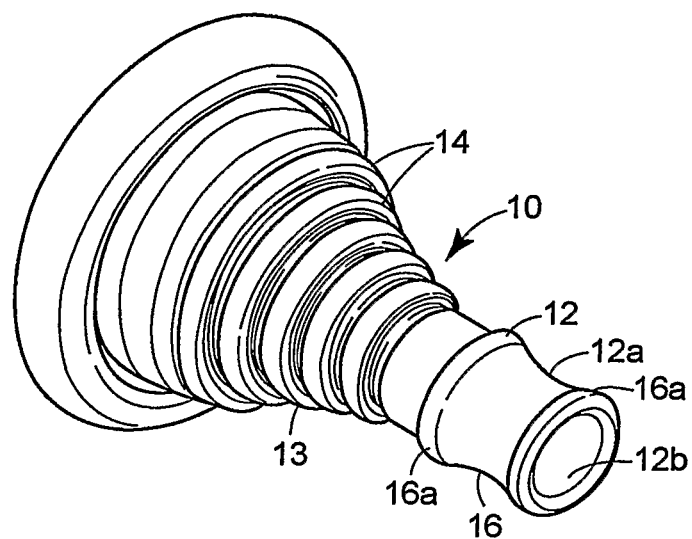
FIG. 3 is a perspective view of the catheter in completed and rolled condition.

Referring to FIGS. 1 and 2 of the drawings, the numeral (10) generally designates a male external catheter injection molded in whole or in part from one or more injection-moldable plastic materials and having an elongated cylindrical body section (11) a drain tube section (12), and a tapered funnel or neck section (13) interposed between and joining the body and drain tube sections. If desired, the body section may have a bulbous portion (11a) at its distal end, such portion serving both as a glans-receiving chamber for enhancing wearer comfort and as an expandable surge chamber for temporarily accommodating surges of fluid that may occur at the commencement of urination.

In the illustration given, the sections of the external catheter are integrally formed, but as explained hereinafter, certain sections such as the drainage tube section may be injection molded as a separate component and joined to the remainder of the catheter through overmolding or multi-shot injection molding.

A distinguishing feature of the external catheter is that its tapered neck section (15) has inner and outer surfaces of substantially different contours. Specifically, the outer surface (13a) is corrugated or convoluted with a longitudinal series of concentric ridges (14) and grooves (15) that diminish in circumferential dimensions towards the distal end of the catheter. The main purpose of the convolutes is to allow flexing of the neck section of the catheter without kinking and occluding its lumen. While the use of such convolutes is known in the prior art, it is believed novel and unobvious that the inner surface (13b) of this same neck section is smooth and free of corrugations. Thus, while the neck section shares the kink-resisting attributes of prior constructions, it does so without providing internal grooves or recesses that might entrap and retain small amounts of urine. The smooth internal surface (13b) of the neck section promotes fluid flow and avoids the potential problem of retaining urine close to the penis when the product is worn.

The external convolutes are shown in the drawings as being smoothly rounded, but it is to be understood that any of a variety of different profiles may be selected for such external corrugations. For example, each of the corrugations of the series may be V-shaped in outline or, alternatively, have sharply-squared edges. Further, while the neck section will generally have a multiplicity of such corrugations or convolutes, the number is not critical and may vary widely depending on the construction and design of the catheter.

As shown most clearly in FIGS. 1 and 2, the drain tube section (12) may also have an outer surface (12a) of substantially different contour than its inside surface (12b). Ideally, the inside surface is cylindrical and merges smoothly with the inner surface of the tapered neck section (13). In prior external catheters, the outer surfaces are also generally cylindrical in shape and, since such drain tube sections must usually be pushed onto stepped connectors for attaching the catheters to tubing leading to urine collection bags, the smoothness of the outer surfaces may make prior drain tube sections difficult to grip and push over such connectors. In contrast, the outer surface (12a) of this drain tube section has one or more annular indentations or recesses (16) and/or one or more annular projections (16a) to provide user-friendly gripping means to facilitate tube attachment. Further, the outer surface of the drain tube section may be textured to further reduce the possibility that the drain tube section might unintentionally slip between the fingers during an attaching operation.

The inner surface of the generally cylindrical body portion (11) may be provided with an annular band or layer (17) of a suitable pressure-sensitive non-allergenic adhesive. Such an adhesive layer may be formed as part of the molding operation, as by overmolding the material of the catheter over an adhesive layer or by introducing the adhesive in the first step of a multi-shot injection molding operation. To enhance adhesion of the adhesive to the catheter, as well as to promote user comfort, the inner surface of the body section may also be textured. Since the catheter is intended to be rolled up in one of the final steps of its manufacture (see FIG. 3), the catheter's outer surface, or at least the outer surface of the cylindrical body section (11) must be coated or otherwise provided with a suitable release material. Silicone rubber has been commonly used in the past to prevent adhesive from adhering to the outer surface of a rolled-up catheter, but any suitable release agent in the form of a layer, coating, or film capable of preventing such adherence may be used. Again, the outer surface of the body section may be textured to promote adhesion between the release material and the body section's outer surface.

Figure 4:
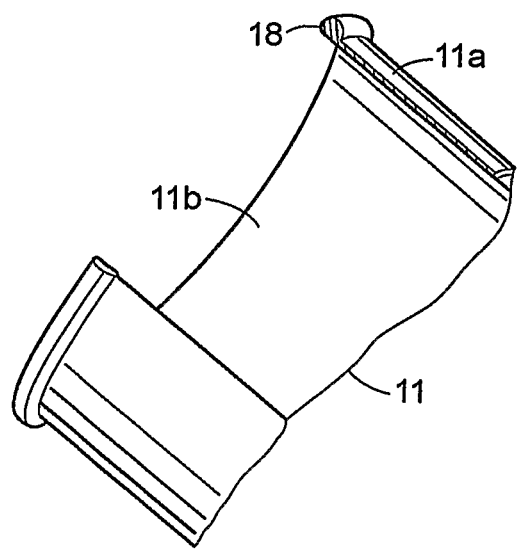
FIG. 4 is a fragmentary perspective view of a second embodiment showing an annular bead formed at the proximal end of the catheter.

FIG. 4 shows that the outer surface (11a) of the cylindrical body section (11) may also depart from the contour of inner surface (11b). Specifically, an annular bead (18) may be provided at the catheter's proximal end. The provision of such a bead facilitates rolling of the sheath at the time of manufacture and when the catheter is to be removed from a patient.

The substantial differences in contour between the inner and outer surfaces of the external catheter are achieved because the catheter is injection molded in its entirety. Any suitable injection-moldable materials or combinations of materials that are preferably soft and flexible may be used. While thermoplastic resins are believed particularly suitable, including thermoplastic elastomers, the injection-moldable material(s) may also include silicones and thermoformable rubbers and vulcanites.

Styrene-type thermoplastic elastomers are believed to be especially suitable and include styrene/butadiene block copolymers (SBS), styrene/isoprene block copolymers (SIS) and the hydrogenation products thereof, styrene/ethylene/butylene block copolymers (SEBS), styrene/ethylene/propylene block polymers (SEPS), styrene/butadiene rubber (SBR) and styrene/butadiene/methyl methacrylate copolymers (MBS). Various additives such as plasticizers, antioxidants, ultraviolet absorbers, light stabilizers, adhesion promoting agents, antibacterial agents, agents for skin conditioning and care, and colorants may be included in the resin composition(s), all as well-known in the art.

Figure 5:
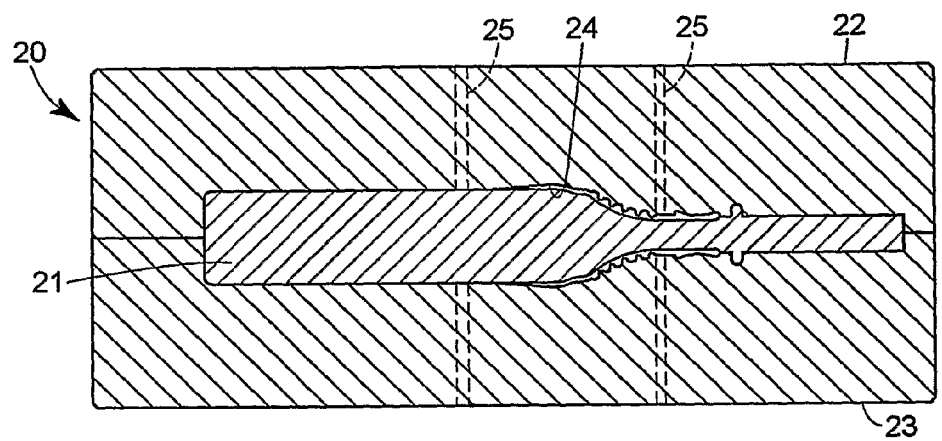
FIG. 5 is a sectional longitudinal view depicting the mandrel and the outer mold sections for injection molding the catheter.
Figure 6:
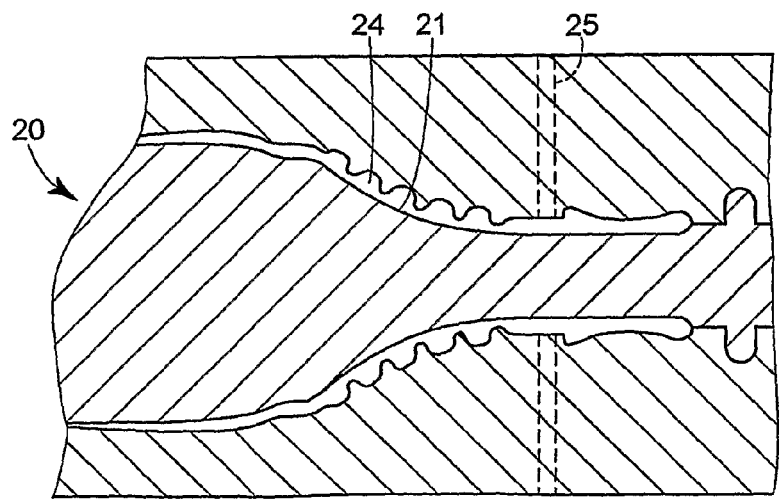
FIG. 6 is an enlarged view of the mandrel and mold elements for forming the final-shaped neck section and contoured drain tube section of the catheter.

FIG. 5 depicts a mold assembly (20) that may be used for injection molding the male external catheter of this invention. The mold includes a mandrel (21) that has an outer surface defining the generally smooth (including evenly textured) inner surface of the final product. The assembly also includes separable mold sections (22) and (23) which together provide a cavity (24) that defines the contoured outer surface of the product. A plurality of inlet passages (25) extend through the mold sections to convey molten plastic material to cavity (24). Once the molten plastic has cooled within the cavity, sections (22) and (23) are separated and the mandrel (21) with the molded catheter supported thereon is advanced for further processing. This may include processing steps that are performed while the catheter remains on the mandrel or, if desired, the catheter may be removed and transferred to a working mandrel.

Figure 7:
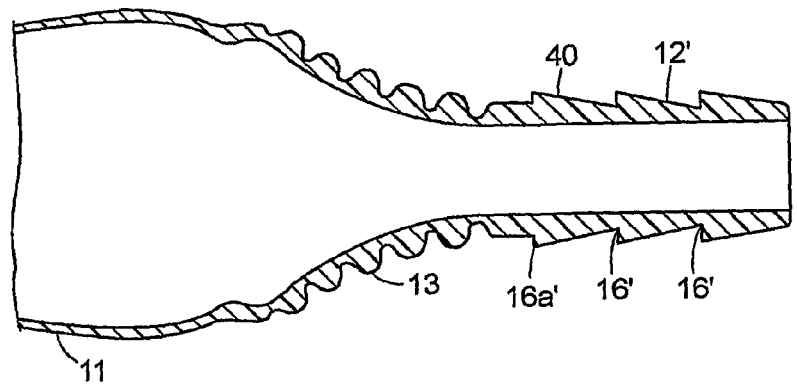
FIG. 7 is a fragmentary longitudinal sectional view of a further embodiment of the invention.

As already described in connection with the embodiment depicted in FIGS. 1-3, the contour of the outer surface of the drain tube section (12) may be provided with one or more recesses (16) and/or projections (16a) to facilitate gripping of the drainage tube section when it is to be coupled to a suitable connector. In the embodiment of FIG. 7, the drainage tube section (12') is provided with a plurality of recesses (16') defined by a series of stepped frusto-conical surface portions (40). The recesses (16') also facilitate the gripping of the drainage tube portion (12') when it is to be fitted upon a suitable connector. However, the illustrated construction might also be used by inserting the drainage tube section into an elastomeric connecting tube, with the drain tube section then being internal to the connecting tube and the edges of the frusto-conical portions serving as barbs to restrain the parts from unintentional separation.

Where the drain tube section is intended to function as the male element in its assembly with a female connector, it is desirable that the drain tube section be stiffer or more rigid that the remainder of the catheter. That may be accomplished by what is known in the art as multi-shot injection molding where, in this instance, the thermoplastic material from which the drain tube section is molded is harder or has a higher elastic modulus than the elastomeric material used for injection molding the remainder of the catheter. Both materials in molten state may be injected simultaneously or sequentially into the cavity (multi-shot injection), and the thermoplastic compatibility of the two materials ensures that the final injection-molded product will have its drain tube section fully integrated with the neck and body sections of the catheter.

Figure 8:
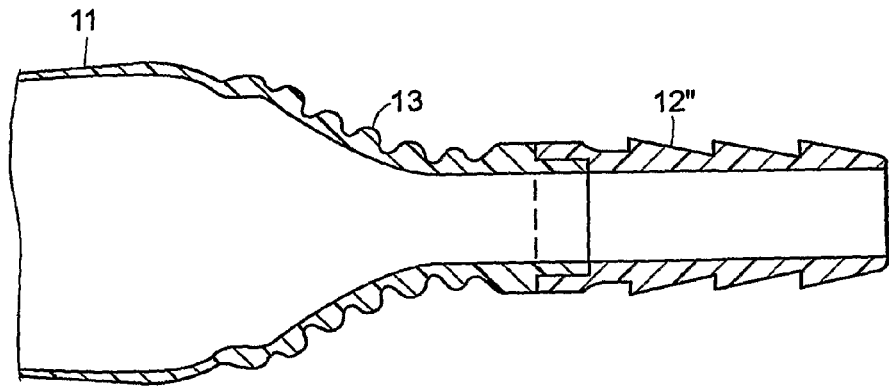
FIG. 8 is a sectional view of a catheter formed by overmolding or multi-shot injection molding with different materials used for the drainage tube section, on one hand, and the sheath and neck sections on the other.

Alternatively, the drain tube section of the catheter may be pre-formed by injection molding in a prior step and then joined in a second injection molding step to the elastomeric neck and body sections. FIG. 8 shows a drain tube section (12") which is preformed of suitable thermoplastic material and placed within the cavity (24) of the mold with softer elastomeric material then being injected to form the stretchable and recoverable neck and body sections (13) and (11). The result is an integrated assembly produced by over-molding in the second injection-molding step.

The sections of the catheter may also differ in respects other than stiffness and stretchability. For example, the drain tube section may be more opaque, or of a different color, than the neck and body sections. Preferably, the neck and body sections are relatively transparent or clear, whereas transparency is less needed for the drain tube section.

Figure 9:
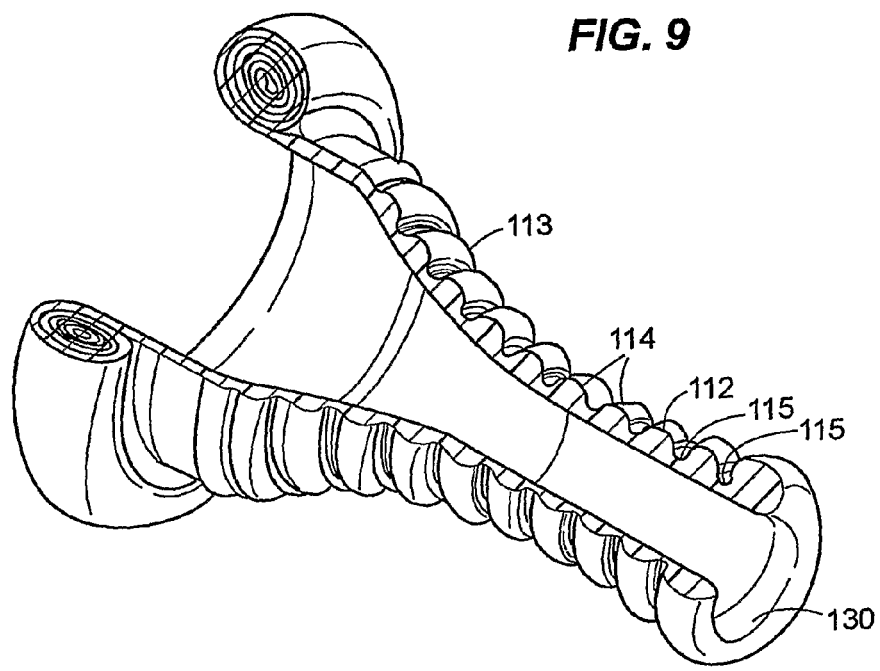
FIG. 9 is a perspective view, partly broken away to reveal longitudinal sectional contours, of a male external catheter constituting a further embodiment of this invention.

FIG. 9 depicts another embodiment of an injection molded catheter embodying the invention. Both the neck section (113) and the drain tube section (112) have their outer surfaces provided with an uninterrupted series of corrugations or convolutions defined by concentric ridges (114) and grooves (115). It will also be noted that the ridges increase slightly in radial thickness, and the grooves become deeper, towards the distal tip of the catheter. If desired, the final ridge or rib may have a chamfered inner surface at (130) to facilitate fitting the drain tube section over the end of a drain tube connector. The corrugations not only enhance non-kinking flexing and bending of the tapered neck and drain tube sections but also provide a gripping surface to facilitate coupling of the catheter to a connector. As in the previous embodiments, the inner surfaces of the neck and drain tube sections are without corrugations and merge smoothly together to promote fluid flow and avoid the grooves and indentations of prior constructions that tend to collect and retain small amounts of fluid in use.

Throughout this application, the term "plastic" has been used in a broad sense to mean a material capable of being molded and then passing into a more solid state because of cooling or curing or some other treatment or condition. In most cases, a thermoplastic material is used, particularly a thermoplastic elastomer, but this invention also comprehends the use of a multi-component composition which passes from a flowable state to a stable or cured state because of a chemical reaction between such components.

While in the foregoing we have disclosed embodiments of the invention in considerable detail for purposes of illustration, it will be understood by those skilled in the art that many of these details may be varied without the departing from the spirit and scope of the invention.

What is claimed is:

1. A one-piece male external catheter comprising a generally cylindrical body section having a substantially constant diameter, a drain tube section of smaller cross section than said generally cylindrical body section for attachment to a drainage tube, and a funnel-shaped section interposed between said generally cylindrical body and drain tube sections wherein the funnel-shaped section includes an inner surface that smoothly merges with an inner surface of the drain tube section and the inner surfaces of the funnel-shaped and drainage tube sections are free of recesses, the funnel-shaped section has an outer surface of substantially different contour than the inner surface, and wherein the outer surface of said funnel-shaped section has corrugations in the form of a longitudinal series of concentric ridges and grooves and the inner surface is free of corrugations.

2. The catheter of claim 1 in which said drain tube section has inner and outer surfaces of substantially different contours.

3. The catheter of claim 2 in which said drain tube section has an outer surface contoured to provide at least one annular recess and/or projection to facilitate manually gripping and coupling of said catheter to said drainage tube.

4. The catheter of claim 3 in which said outer surface of said drain tube section has a series of longitudinally-spaced annular recesses and projections.

5. The catheter of claim 1 in which said catheter is made from a thermoplastic material.

6. The catheter of claim 5 in which said thermoplastic material is an elastomer.

7. The catheter of claim 6 in which said drain tube section is formed of a thermoplastic material compatible with the thermoplastic elastomer of said funnel-shaped and generally cylindrical body sections but being stiffer and less stretchable than said elastomer.

8. The catheter of claim 4 in which said longitudinally-spaced recesses and projections of said outer surface of the drainage tube are frusto-conical in shape.

9. The catheter of claim 1 in which said generally cylindrical body section defines an opening at the proximal end of said catheter; said inner surface of said generally cylindrical body section being generally cylindrical in shape and said outer surface of said generally cylindrical body section having an annular outwardly-projecting bead at its proximal end.

10. The catheter of claim 1 in which at least one of said catheter sections is composed of inner and outer layers of different but compatible injection-moldable materials.

11. The catheter of claim 10 in which said material of said outer layer includes a release agent.

12. The catheter of claim 11 in which said material of said inner layer includes an adhesive.

13. The catheter of claim 1 in which at least one of said inner and outer surfaces of at least one of said sections is textured.

14. A method of making a one-piece male external catheter as called for in claim 1 comprising the steps of:
   providing a mandrel having outer surfaces defining the inner surfaces of said catheter;
   providing a mold with separable sections forming a mandrel-receiving cavity with inner surfaces defining the outer surfaces of said catheter;
   an inner surface portion of said cavity defining the outer surface of said funnel-shaped section with annular corrugations in the form of a series of concentric ridges and grooves;
   and an outer surface portion of said mandrel defining the inner surface of said funnel-shaped section as smoothly tapered without corrugations;
   injecting into said cavity at least one molten injection-moldable plastic material capable of cooling into a solid state;
   and thereafter allowing said material to cool, separating said mold sections, and removing the one-piece catheter from said cavity.

15. The method of claim 14 in which said mandrel has a portion of its outer surface defining the inner surface of said drain tube section as being of smooth cylindrical shape; said cavity having portions thereof defining the outer surface of said drain tube section with at least one annular recess and/or projection for facilitating manual gripping of said catheter.

16. The method of claim 14 in which said mandrel has a cylindrical outer surface portion defining the inner surface of said catheter's generally cylindrical body section; said cavity defining the outer surface of said generally cylindrical body section with an annular recess for forming an external bead at the proximal end of said catheter.

17. The method of claim 14 in which said injection-moldable material is thermoplastic.

18. The method of claim 17 in which at least two different but compatible thermoplastic materials are injected into said cavity.

19. The method of claim 18 in which at least one of said thermoplastic materials is elastomeric.

20. The method of claim 19 in which the thermoplastic material for forming said drain tube section has a higher elastic modulus than the thermoplastic material for forming said generally cylindrical body section.

21. The method of claim 18 in which said drainage tube section, and said generally cylindrical body and funnel-shape sections, are formed together by overmolding.

22. The method of claim 18 in which said drain tube section, and said generally cylindrical body and funnel-shape sections, are formed by multi-shot injection molding.

23. A one-piece male external catheter comprising a generally cylindrical body section having a substantially constant diameter, a drain tube section of smaller cross section than said generally cylindrical body section for attachment to a drainage tube, and a funnel-shaped section interposed between said generally cylindrical body and drain tube sections wherein the funnel-shaped section includes an inner surface that smoothly merges with an inner surface of the drain tube section and the inner surfaces of the funnel-shaped and drainage tube sections are free of recesses, the funnel-shaped section has an outer surface of substantially different contour than the inner surface, and
   wherein the generally cylindrical body section includes a bulbous portion for receiving a glans penis at a distal end of the generally cylindrical body section.

24. The catheter of claim 23 in which the outer surface of said funnel-shaped section has corrugations in the form of a longitudinal series of concentric ridges and grooves and the inner surface is free of corrugations.

25. The catheter of claim 23 in which said drain tube section has inner and outer surfaces of substantially different contours.

26. The catheter of claim 25 in which said drain tube section has an outer surface contoured to provide at least one annular recess and/or projection to facilitate manually gripping and coupling of said catheter to said drainage tube.

27. The catheter of claim 26 in which said outer surface of said drain tube section has a series of longitudinally-spaced annular recesses and projections.

28. The catheter of claim 23 in which said catheter is made from a thermoplastic material.

29. The catheter of claim 28 in which said thermoplastic material is an elastomer.

30. The catheter of claim 29 in which said drain tube section is formed of a thermoplastic material compatible with the thermoplastic elastomer of said funnel-shaped and generally cylindrical body sections but being stiffer and less stretchable than said elastomer.

31. The catheter of claim 27 in which said longitudinally-spaced recesses and projections of said outer surface of the drainage tube are frusto-conical in shape.

32. The catheter of claim 23 in which said generally cylindrical body section defines an opening at the proximal end of said catheter; said inner surface of said generally cylindrical body section being generally cylindrical in shape and said outer surface of said generally cylindrical body section having an annular outwardly-projecting bead at its proximal end.

33. The catheter of claim 23 in which at least one of said catheter sections is composed of inner and outer layers of different but compatible injection-moldable materials.

34. The catheter of claim 33 in which said material of said outer layer includes a release agent.

35. The catheter of claim 34 in which said material of said inner layer includes an adhesive.

36. The catheter of claim 23 in which at least one of said inner and outer surfaces of at least one of said sections is textured.

* * * * *